US006303100B1

(12) United States Patent
Ricci et al.

(10) Patent No.: US 6,303,100 B1
(45) Date of Patent: *Oct. 16, 2001

(54) METHODS FOR INHIBITING THE FORMATION OF POTENTIAL ENDOLEAKS ASSOCIATED WITH ENDOVASCULAR REPAIR OF ABDOMINAL AORTIC ANEURYSMS

(75) Inventors: Charlie Ricci, Mission Viejo, CA (US); Bart Dolmatch, Hunting Valley, OH (US); Andrew H. Cragg, Edina, MN (US); Richard J. Greff, St. Pete Beach, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

(21) Appl. No.: 09/273,100

(22) Filed: Mar. 19, 1999

(51) Int. Cl.$^7$ ............................ A61K 51/00; A61M 36/14
(52) U.S. Cl. ...................... 424/1.29; 424/1.73; 424/1.65; 424/9.1
(58) Field of Search .................................. 424/1.11, 1.29, 424/1.65, 1.73, 9.1, 422

(56) References Cited

U.S. PATENT DOCUMENTS

| | | |
|---|---|---|
| 3,527,224 | 9/1970 | Rabinowitz . |
| 3,591,676 | 7/1971 | Hawkins et al. . |
| 4,795,741 | 1/1989 | Lishchiner et al. . |
| 4,938,763 | 7/1990 | Dunn et al. . |
| 5,580,568 | 12/1996 | Greff et al. . |
| 5,667,767 | 9/1997 | Greff et al. . |
| 5,695,480 | 12/1997 | Evans et al. . |
| 5,702,361 | 12/1997 | Evans et al. . |
| 5,749,894 | 5/1998 | Engelson . |
| 5,749,922 | 5/1998 | Slepian . |
| 5,868,778 | 2/1999 | Gershony et al. . |

FOREIGN PATENT DOCUMENTS

| | | |
|---|---|---|
| 06107549 | 4/1994 | (JP) . |

OTHER PUBLICATIONS

White et al., Endoleak as a Complication of Endoluminal Grafting of Abdominal Aortic Aneurysms: Classification, Incidence, Diagnosis, and Management. J. Endovasc. Surg. 1997, 4, pp. 152–168.*

Mialhe et al, Endovascular treatment of infrarenal abdominal aneurysms by the stentor system: Pet. Preliminary results of 79 cases. J. Vascu. Surg. 1997, 26, pp. 199–209.*

Schie et al, Successful Embolization of Persistent Endoleak From a Patent Inferior System, J. Endovasc. Surgy., vol. 4 pp. 312–315, 1997.*

Walker et al, A Study on the Patency of the Inferior Mesenteric and Lumbar Arteries in the Incidence of Endoleak Following Endovascular Repair of Infra–renal Aortic Aneurysms. Clinical Radiology (1998), vol. 53, pp. 593–595.*

Broeders, et al., "The Role of Infrarenal Aortic Side Branches in the Pathogenesis of Endoleaks after Endovascular Aneurysm Repair", *Eur. J. Vasc. Endovasc. Surg.*, 16: 419–426 (1998).

Holzenbein, et al., "Endovascular Management of "Endoleaks" After Transluminal Infrarenal Abdominal Aneurysm Repair", Eur. J. Vasc. Endovasc. Surg., 16: 208–217 (Sep., 1998).

Karch, et al., "Algorithm for the Diagnosis and Treatment of Endoleaks", Am. J. Surg., 178: 225–231 (1999).

Wain, et al., "Endoleaks after Endovascular Graft Treatment of Aortic Aneurysms: Classification, Risk Factors, and Outcome", J. Vasc. Surg., 27: 69–80 (1998).

Registry CopyRight 2000 ACS 6606–65–1 Registry files (May 2000).

Registry CopyRight 2000 ACS 25154–80–7 Registry files (May 2000).

Registry CopyRight 2000 ACS 87435–86–7 Registry files (May 2000).

Registry CopyRight 2000 ACS 79817–44–0 Registry files (May 2000).

Registry CopyRight 2000 ACS 12619–85–1 Registry files (May 2000).

U.S. application No. 08/802,252, Evans et al., filed Feb. 19, 1997.

Beebe, et al., "Current Status of the United States Vanguard™ Endograft Trial", JPVA 2.1–2.3, Presented at the 6$^{th}$ Annual Symposium on Current Issues and New Techniques in Interventional Radiology at New York, New York in Nov., 1998.

Castaneda–Zuniga, et al., *Interventional Radiology*, in Vascular Embolotherapy, Part 1, 1:9–32, Williams & Wilkins, Publishers (1992).

Hopkinson, et al., "Current Critical Problems, New Horizons and Techniques in Vascular and Endovascular Surgery", JPIII 4.1–4.2, Presented at the 6$^{th}$ Annual Symposium on Current Issues and New Techniques in Interventional Radiology at New York, New York in Nov., 1998.

(List continued on next page.)

*Primary Examiner*—Dameron L. Jones
(74) *Attorney, Agent, or Firm*—Burns Doane Swecker & Mathis

(57) ABSTRACT

Disclosed are methods for inhibiting the formation of potential endoleaks associated with endovascular repair of abdominal aortic aneurysms which comprise the in situ embolization of blood vessels associated with the aneurysmal sac prior to placement of an endovascular prostheses in the abdominal aorta. Embolization of the blood vessels is achieved by injection of either a biocompatible polymer or prepolymer fluid composition into these vessels in a sufficient amount such that upon in situ solidification of this composition, blood circulation through these blood vessels and the aneurysmal sac ceases.

19 Claims, No Drawings

OTHER PUBLICATIONS

Kinugasa, et al., "Direct Thrombosis of Aneurysms with Cellulose Acetate Polymer", J. Neurosurg., 77:501–507 (1992).

Kinugasa, et al., "Early Treatment of Subarachnoid Hemorrhage After Preventing Rerupture of an Aneurysm", J. Neurosurg., 83:34–41 (1995).

Marty, et al., "Endoleak After Endovascular Graft Repair of Experimental Aortic Aneurysms: Does Coil Embolization with Angiographic "Seal" Lower Intraaneursymal Pressure", J. Vasc. Surg., 27(3):454–462 (1998).

Kinugasa, et al., "Prophylactic Thrombosis to Prevent New Bleeding and to Delay Aneurysm Surgery", Neurosurg., 36:661 (1995).

May, et al., "Concurrent Comparison of Endoluminal Versus Open Repair in the Treatment of Abdominal Aortic Aneurysms: Analysis of 303 Patients by Life Table Method", J. Vasc. Surg. 27(2):213–221 (1998).

Money, et al., "Perioperative Charge Comparison and Endovascular Abdominal Aortic Aneurysm Repair", JPV 1.1–1.2, Presented at the $6^{th}$ Annual Symposium on Current Issues and New Techniques in Interventional Radiology at New York, New York in Nov., 1998.

Parodi, Endovascular AAA Stent Grafts: Technology, Training and Proper Patient Selection, JPVA 1.1–1.2 Presented at the $6^{th}$ Annual Symposium on Current Issues and New Techniques in Interventional Radiology at New York, New York in Nov., 1998.

Taki, et al., "Selection and Combination of Various Endovascular Techniques in the Treatment of Giant Aneurysms", J. Neurosurg., 77:37–42 (1992).

White, et al., "Endoleaks"—A Proposed New Terminology to Describe Incomplete Aneurysm Exclusion by an Endoluminal Graft. J. Endovasc. Surg., 3:124–125 (1996).

\* cited by examiner

METHODS FOR INHIBITING THE FORMATION OF POTENTIAL ENDOLEAKS ASSOCIATED WITH ENDOVASCULAR REPAIR OF ABDOMINAL AORTIC ANEURYSMS

BACKGROUND OF THE INVENTION

FIELD OF THE INVENTION

This invention is directed to methods for inhibiting the formation of potential endoleaks associated with endovascular repair of abdominal aortic aneurysms. In one embodiment, this invention is directed to methods for inhibiting the formation of potential endoleaks arising either from retrograde bleeding from blood vessels associated with the aneurysmal sac such as the lumbar and inferior mesenteric arteries into the aneurysm sac or from potential defects within the endovascular prosthesis which permit blood flow through it after endovascular repair of abdominal aortic aneurysms. Specifically, the methods of this invention involve the in situ embolization of blood vessels associated with the aneurysmal sac prior to placement of an endovascular prostheses in the abdominal aorta. Embolization of the blood vessels is achieved by injection of either a biocompatible polymer or prepolymer fluid composition into these vessels in a sufficient amount such that upon in situ solidification of this composition, blood circulation through these blood vessels and the aneurysmal sac ceases. Preferably, the biocompatible fluid composition comprises a contrast agent to allow the clinician to visualize the embolization process.

In another embodiment, the methods of this invention further comprise sealing of endoleaks formed after placement of the endovascular prosthesis by injection of either a biocompatible polymer or prepolymer fluid composition at the site of the endoleak which composition in situ solidifies and adheres to the vascular and/or prosthetic wall to seal the leak. Preferably, the biocompatible fluid composition comprises a contrast agent to allow the clinician to visualize the sealing process.

REFERENCES

The following publications, patent applications and patents are cited in this application as superscript numbers:

[1] May, et al., "Concurrent Comparison of Endoluminal Versus Open Repair in the Treatment of Abdominal Aortic Aneurysms: Analysis of 303 Patients by Life Table Method", J. Vasc. Surg. 27(2):213–221 (1998)

[2] White, et al., J. Endovasc. Surg., 3:124–125 (1996)

[3] Marty, et al., "Endoleak After Endovascular Graft Repair of Experimental Aortic Aneurysms: Does Coil Embolization with Angiographic "Seal" Lower Intraaneursymal Pressure", J. Vasc. Surg., 27(3):454–462 (1998)

[4] Money, et al., "Perioperative Charge Comparison and Endovascular Abdominal Aortic Aneurysm Repair", JPV 1.1–1.2, Presented at the 6$^{th}$ Annual Symposium on Current Issues and New Techniques in Interventional Radiology at New York, N.Y. in November, 1998

[5] Beebe, et al., "Current Status of the United States Vanguard™ Endograft Trial", JPVA 2.1–2.3, Presented at the 6$^{th}$ Annual Symposium on Current Issues and New Techniques in Interventional Radiology at New York, N.Y. in November, 1998

[6] Hopkinson, et al., "Current Critical Problems, New Horizons and Techniques in Vascular and Endovascular Surgery", JPIII 4.1–4.2, Presented at the 6$^{th}$ Annual Symposium on Current Issues and New Techniques in Interventional Radiology at New York, N.Y. in November, 1998

[7] Kinugasa, et al., "Direct Thrombosis of Aneurysms with Cellulose Acetate Polymer", J. Neurosurg., 77:501–507 (1992)

[8] Greff, et al., U.S. Pat. No. 5,667,767 for "Novel Compositions for Use in Embolizing Blood Vessels", issued Sep. 16, 1997

[9] Greff, et al., U.S. Pat. No. 5,580,568 for "Cellulose Diacetate Compositions for Use in Embolizing Blood Vessels", issued Dec. 3, 1996

[10] Kinugasa, et al., "Early Treatment of Subarachnoid Hemorrhage After Preventing Rerupture of an Aneurysm", J. Neurosurg., 83:34–41 (1995)

[11] Kinugasa, et al., "Prophylactic Thrombosis to Prevent New bleeding and to Delay Aneurysm Surgery", Neurosurg., 3:661 (1995)

[12] Taki, et al., "Selection and Combination of Various Endovascular Techniques in the Treatment of Giant Aneurysms", J. Neurosurg., 77:37–42 (1992)

[13] Evans, et al., U.S. patent application Ser. No. 08/802, 252 for "Novel Compositions for Use in Embolizing Blood Vessels", filed Feb. 19, 1997.

[14] Castaneda-Zuniga, et al., Interventional Radiology, in Vascular Embolotherapy, Part 1, 1:9–32, Williams & Wilkins, Publishers (1992)

[15] Rabinowitz, et al., U.S. Pat. No. 3,527,224, for "Method of Surgically Bonding Tissue Together", issued Sep. 8, 1970

[16] Hawkins, et al., U.S. Pat. No. 3,591,676, for "Surgical Adhesive Compositions", issued Jul. 6, 1971

[17] Parodi, "Endovascular AAA Stent Grafts: Technology, Training and Proper Patient Selection, JPVA 1.1–1.2 Presented at the 6$^{th}$ Annual Symposium on Current Issues and New Techniques in Interventional Radiology at New York, N.Y. in November, 1998

All of the above publications, patent applications and patents are herein incorporated by reference in their entirety to the same extent as if each individual publication, patent application or patent was specifically and individually indicated to be incorporated by reference in its entirety.

State of the Art

Abdominal aortic aneurysms (AAA) represents a serious medical challenge and, when left untreated, eventual rupture of the aneurysm has significant morbidity associated therewith. When feasible, open surgery to repair the aortic aneurysm has been shown to be clinically successful.[1] However, open surgery is often not feasible especially in patients suffering from severe cardiac disease, renal disease or other conditions which contraindicate open surgery. For example, conventional exposure of the infrarenal aorta necessitates a large abdominal incision, mobilization of the abdominal viscera, and retroperitoneal dissection which are associated with complications such as renal failure, pseudoaneurysms and bleeding. Infrarenal aortic clamping is also associated with an increased cardiac demand including an increase in left ventricular end diastolic volume and may be related to cardiac mortality.

Less invasive methods for treating abdominal aortic aneurysms avoid many of these problems and additionally result in reduced patient discomfort, reduced hospital stays and reduced care intensity.[5] Endovascular grafts have been investigated as one example of a less invasive method for the treatment of aneurysmal aortic disease. When compared to open surgery, endovascular grafting provides similar perioperative mortality rates notwithstanding the fact that endovascular grafting is often performed with individuals who are not candidates for open surgery due to one or more medical conditions which preclude such surgery.[1,4] One of the main concerns regarding endovascular grafting is the continued blood flow into the aneurysm after grafting which blood flow is termed in the art as an endoleak.[2] Endoleaks have been reported in about 7 and 37% of endovascular aortic aneurysm repairs[3] with some reports placing this number as high as 44%.

Specifically, endovascular grafting requires catheter placement of an endovascular prostheses at the abdominal aortic aneurysm site. Endoleaks arising after such grafting may be caused by incomplete sealing between the endovascular prosthesis and the aortic wall or by defects within the endovascular prostheses. In addition, retrograde bleeding from patent lumbar and inferior mesenteric arteries following placement of the endovascular prostheses in the aorta has also been recited as a potential cause of endoleaks.[6] There is uniform agreement that large endoleaks that lead to aneurysm enlargement necessitate treatment in order to prevent aneurysm rupture. It is also reported that the size of the endoleak does not appear to be a relevant factor for pressure transmission into the aneurysm.[3]

There are a variety of treatment regimens for endoleaks reported in the literature including endovascular repair by placement of additional stents within the prostheses as well as insertion of metallic coils into the aneurysm space to induce thrombosis therein. The goal of such treatments is complete exclusion of the aneurysm from systemic blood flow. While complete exclusion is desirable, a secondary goal is to reduce intraaneursymal pressure (IAP) from blood flow into the aneurysm to acceptable levels thereby inhibiting the likelihood of rupture. In cases where no endoleaks arose after endovascular grafting, the mean IAP has been reported to be reduced by about 65%. However, when endoleaks arise, it is reported that the mean IAP, while initially decreasing significantly, stabilized after a week at a reduction of only 22%. Moreover, the use of coils to induce thrombosis and thereby reduce IAP did not have any significant impact on the IAP.

In view of existing problems associated with endovascular repair of endoleaks, the accepted treatment for these endoleaks is open surgery. However, the mortality rates for open surgery of endoleaks is higher than either initial open surgery for the abdominal aortic aneurysm or for the initial endovascular repair of the aneurysm.

In view of the above, reliable endovascular methods to inhibit endoleaks associated with endovascular graft repair of abdominal aortic aneurysms is desirable. The methods of the present invention fulfills this need.

SUMMARY OF THE INVENTION

This invention is directed to methods for inhibiting the formation of potential endoleaks arising from endovascular repair of abdominal aortic aneurysms.

In one aspect, the methods of this invention comprise inhibiting the formation of potential endoleaks arising either from retrograde bleeding from blood vessels associated with the aneurysmal sac such as the lumbar and inferior mesenteric arteries into the aneurysm sac or from potential defects within the endovascular prosthesis which permit blood flow through it after endovascular repair of abdominal aortic aneurysms.

Specifically, the methods of this invention involve the in situ embolization of blood vessels associated with the aneurysmal sac prior to placement of an endovascular prostheses in the abdominal aorta. Embolization of the blood vessels is achieved by injection of either a biocompatible polymer or prepolymer fluid composition into these vessels in a sufficient amount such that upon in situ solidification of this composition, blood circulation through these blood vessels and the aneurysmal sac ceases. Preferably, the biocompatible fluid composition comprises a contrast agent to allow the clinician to visualize the embolization process.

In another aspect, the methods of this invention further comprise sealing of endoleaks formed after placement of the endovascular prosthesis by injection of a biocompatible fluid composition at the site of the endoleak which composition in situ forms a coherent solid mass which adheres to vascular and/or prosthetic wall to seal the endoleak. These methods are described in Applicants' application, U.S. Ser. No.09/273,120, filed concurrently herewith on Mar. 19, 1999, as Attorneys docket No. 018413–185 which is entitled "Methods For Treating Endoleaks During Endovascular Repair of Abdominal Aortic Aneurysms" which application is incorporated herein by reference in its entirety. In a preferred embodiment, the fluid composition comprises a biocompatible polymer, a biocompatible solvent and a contrast agent to allow the clinician to visualize the procedure.

In a further preferred embodiment, the contrast agent is a water insoluble contrast agent characterized by having an average particle size of about 10 $\mu$m or less.

In another preferred embodiment, the fluid composition comprises a biocompatible prepolymer and a contrast agent which, again, is employed to allow the clinician to visualize the procedure. In a further preferred embodiment, the contrast agent is a water insoluble contrast agent characterized by having an average particle size of about 10 $\mu$m or less.

Accordingly, in one of its method aspects, this invention provides a method for inhibiting the formation of potential endoleaks in a patient arising from endovascular repair of abdominal aortic aneurysms which method comprises:

identifying an abdominal aortic aneurysm in a patient;

embolizing blood vessels associated with the aneurysmal sac wherein said embolization comprises delivering through a microcatheter a sufficient amount of a biocompatible fluid composition to said vessels under conditions where the fluid composition solidifies thereby embolizing said vessels and;

subsequently endovascularly repairing said aneurysm by catheter delivery of an endovascular prosthesis to the site of said aneurysm thereby inhibiting blood flow into the aneurysm.

Methods further comprising the step of delivering a detectable agent, such as a contrast agent, through the catheter after it has been inserted into the blood vessels capable of delivering blood flow to the aneurysm sac and detecting the agent to confirm that the catheter has the proper placement prior to delivery of the fluid composition to the blood vessels are also provided.

DETAILED DESCRIPTION OF THE INVENTION

This invention is directed to novel methods for inhibiting the formation of potential endoleaks associated with endovascular repair of abdominal aortic aneurysms. In particular, this invention is directed to methods for inhibiting the formation of potential endoleaks arising either from retrograde bleeding from blood vessels associated with the aneurysmal sac such as the lumbar and inferior mesenteric arteries into the aneurysm sac or from potential defects within the endovascular prosthesis which permit blood flow through it after endovascular repair of abdominal aortic aneurysms.

Specifically, the methods of this invention involve the in situ embolization of blood vessels associated with the aneurysmal sac prior to placement of an endovascular prostheses in the abdominal aorta. Embolization of the blood vessels is achieved by injection of either a biocompatible polymer or prepolymer fluid composition into these vessels in a sufficient amount such that upon in situ solidification of this composition, blood circulation through these blood vessels and the aneurysmal sac ceases.

However, prior to discussing this invention in further detail, the following terms will first be defined:

The term "embolizing blood vessels" refers to a process wherein a biocompatible fluid composition is injected into the blood vessels such that upon in situ solidification of this composition, blood flow through these vessels and the aneurysmal sac ceases. For example, embolization of patent lumbar and/or the inferior mesenteric arteries stops the flow of blood to or from these vessels to the aneurysmal sac.

The term "biocompatible polymer" refers to polymers which, in the amounts employed, are non-toxic, chemically inert, and substantially noninmnunogenic when used internally in the patient and which are substantially insoluble in blood. Suitable biocompatible polymers include, by way of example, cellulose acetates[7,10-11] (including cellulose diacetatel[9]), ethylene vinyl alcohol copolymers[8,12], hydrogels (e.g., acrylics), polyacrylonitrile, polyvinylacetate, cellulose acetate butyrate, nitrocellulose, copolymers of urethanelcarbonate, copolymers of styrene/maleic acid, and mixtures thereof.[13] Preferably, the biocompatible polymer does not induce chronic inflammation when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the sealing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in sealing endoleaks arising from endovascular repair of an abdominal aortic aneurysm.

The term "contrast agent" refers to a biocompatible (non-toxic) radiopaque material capable of being monitored during injection into a mammalian subject by, for example, radiography or fluoroscopy. The contrast agent can be either water soluble or water insoluble. Examples of water soluble contrast agents include metrizamide, iopamidol, iothalamate sodium, iodomide sodium, and meglumine.

The term "water insoluble contrast agent" refers to a water insoluble (i.e., has a water solubility of less than 0.01 mg/mil at 20° C.), radiopaque material capable of being monitored during injection into a mannnalian subject by, for example, radiography or fluoroscopy. Examples of water insoluble contrast agents include tantalum, tantalum oxide and barium sulfate, which are commercially available in the proper form for in vivo use. Methods for preparing such water insoluble biocompatible contrast agents having an average particle size of about 10 $\mu$m or less are described below. Other water insoluble contrast agents include gold, tungsten and platinum.

The term "biocompatible solvent" refers to an organic material liquid at least at body temperature of the mammal in which the biocompatible polymer is soluble and, in the amounts used, is substantially non-toxic. Suitable biocompatible solvents include, by way of example, ethanol, acetone, dimethylsulfoxide, analogues/homologues of dimethylsulfoxide, ethyl lactate, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide (DMSO).

The term "encapsulation" as used relative to the contrast agent being encapsulated in the polymer precipitate is not meant to infer any physical entrapment of the contrast agent within the precipitate such as a capsule encapsulates a medicament. Rather, this term is used to mean that an integral coherent precipitate forms which does not separate into individual components.

The term "adheres to" as used herein means that the composition formed in situ retains the position/location where the polymer mass formed after injection and thereby functions to seal the blood vessels. This term does not necessarily infer that the composition acts as an adhesive although in the case of, for example, a cyanoacrylate prepolymer, the solid composition formed may, in fact, be adhesive.

The term "biocompatible prepolymer" refers to materials which polymerize in situ to form a polymer and which, in the amounts employed, are non-toxic, chemically inert, and substantially non-immunogenic when used internally in the patient and which are substantially insoluble in blood. Suitable biocompatible prepolymers include, by way of example, cyanoacrylates[14,15,16], hydroxyethyl methacrylate, silicone prepolymers, and the like. The prepolymer can either be a monomer or a reactive oligomer[16]. Preferably, the biocompatible prepolymer does not induce chronic inflammation when employed in vivo.

Compositions

The compositions used in the methods of this invention are biocompatible fluid compositions characterized by the fact that these compositions form a coherent mass in vivo which adheres to the vascular wall of the blood vessels thereby ceasing the blood flow through these vessels and the aneurysmal sac. The fluid compositions employed in the methods of this invention are polymer or prepolymer compositions prepared by conventional methods whereby each of the components is added and the resulting composition mixed or stirred together until the overall composition is substantially homogeneous.

Fluid polymer compositions preferably comprise a biocompatible polymer, a biocompatible solvent and optionally a contrast agent. Such compositions can be prepared by adding sufficient amounts of the biocompatible polymer to the biocompatible solvent to achieve the effective concentration for the polymer composition. Preferably, the polymer composition will comprise from about 2.5 to about 12.0 weight percent of the biocompatible polymer composition based on the total weight of the polymer composition and more preferably from about 4 to about 5.4 weight percent. If necessary, gentle heating and stirring can be used to effect dissolution of the biocompatible polymer into the biocompatible solvent, e.g., 12 hours at 50° C.

When employed, sufficient amounts of the contrast agent are then added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 weight percent. Insofar as the contrast agent may not be soluble in the biocompatible solvent (e.g., a water insoluble contrast agent), stirring is employed to effect homogeneity of the resulting suspension.

In order to enhance formation of the suspension, the particle size of the water insoluble contrast agent is preferably maintained at about 10 $\mu$m or less and more preferably at from about 1 to about 5 $\mu$m (e.g., an average size of about 2 $\mu$m). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

When no contrast agent is employed, the biocompatible solvent is preferably employed at a concentration of from 88 to about 97.5 weight percent of the biocompatible polymer composition based on the total weight of the polymer composition and more preferably from about 90 to about 95 weight percent.

When a contrast agent is employed, the biocompatible solvent is preferably employed at a concentration of from 52 to 87.5 weight percent based on the total weight of the composition; more preferably from about 54.8 to about 76 weight percent; and even more preferably 64.8 to about 66 weight percent. Typical examples of suitable concentrations of individual components are given in the table below:

| Example | Polymer | Solvent | Contrast Agent |
| --- | --- | --- | --- |
| A | 2.5 weight % | 97.5 weight % | — |
| B | 8 weight % | 92 weight % | — |
| C | 2.5 weight % | 87.5 weight % | 10 weight % |
| D | 8 weight % | 82 weight % | 10 weight % |
| E | 2.5 weight % | 57.5 weight % | 40 weight % |
| F | 8 weight % | 52 weight % | 40 weight % |
| G | 8 weight % | 72 weight % | 20 weight % |
| H | 2.5 weight % | 67.5 weight % | 30 weight % |
| I | 8 weight % | 62 weight % | 30 weight % |
| J | 4 weight % | 66 weight % | 30 weight % |
| K | 5.4 weight % | 64.6 weight % | 30 weight % |

The particular order of addition of components to the biocompatible solvent is not critical and stirring of the resulting solution/suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, $\gamma$ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions preferably comprise a biocompatible prepolymer and optionally a contrast agent. When a contrast agent is employed, such compositions can be prepared by adding sufficient amounts of the contrast agent to the solution (e.g., liquid prepolymer) to achieve the effective concentration for the complete composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid, the use of a biocompatible solvent is not absolutely necessary but may be preferred to provide for an appropriate viscosity, etc. in the composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition. Typical examples of suitable concentrations of individual components are given in the table below:

| Example | Polymer | Solvent | Contrast Agent |
| --- | --- | --- | --- |
| L | 100 weight % | — | — |
| M | 90 weight % | — | 10 weight % |
| N | 80 weight % | — | 20 weight % |
| O | 70 weight % | — | 30 weight % |
| P | 60 weight % | — | 40 weight % |
| Q | 70 weight % | 30 weight % | — |
| R | 10 weight % | 90 weight % | — |
| S | 60 weight % | 30 weight % | 10 weight % |
| T | 30 weight % | 30 weight % | 40 weight % |
| U | 40 weight % | 30 weight % | 40 weight % |
| V | 60 weight % | 10 weight % | 30 weight % |

In a particularly preferred embodiment, the prepolymer is a cyanoacrylate ester which is preferably employed in the absence of a biocompatible solvent. When so employed, the cyanoacrylate composition is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Methods

The compositions described above can then be employed in methods for the catheter assisted embolization of blood vessels associated with the aneurysmal sac including lumbar and inferior mesenteric arteries thereby inhibiting the formation of potential endoleaks caused by blood flow between these vessels and the aneurysm sac after endovascular repair of abdominal aortic aneurysms by an endovascular prosthesis.

Specifically, endovascular repair of such aneurysms involves the introduction of an endovascular prosthesis into the abdominal aortic aneurysm which is an art recognized procedure described, for example, by Parodi.[17] This procedure typically consists of dissection of the femoral artery at the groin and introduction of an endovascular prosthesis inside the abdominal aortic aneurysm. Upon insertion, the prosthesis excludes the aneurysm sac thereby repairing the aneurysm. Suitable endovascular prostheses for endovascular repair of abdominal aortic aneurysms are well known in the art and are described, for example, by Beebe, et al.[5] Such prostheses, by themselves, do not form part of this invention. Similarly, catheters for delivering such endovascular prostheses to the site of the abdominal aortic aneurysm are also well known in the art and are commercially available. Such catheters, by themselves, also do not form part of this invention.

In the methods of this invention, a sufficient amount of the fluid composition described above is introduced into the blood vessels via a catheter delivery means preferably under fluoroscopy so that embolization of the blood vessels can be visualized. The specific amount of fluid composition employed is dictated by the total size of the blood vessel, and other factors such as the concentration of polymer/prepolymer in the composition, the rate of solids formation, etc. Such factors are well within the skill of the art.

Prior to sealing the potential endoleak in the manner described above, the clinician would first identify the site or sites of the potential endoleak which typically include lumbar and inferior mesenteric arteries associated with the aneurysm itself.

Access to these sites of blood vessels where the fluid composition is to be delivered can be achieved by endovascular catheter access via the femoral artery which is well known in interventional radiology practice. After access is achieved, delivery of the fluid composition proceeds as described above.

One particularly preferred method for catheter delivering the compositions described in the methods of this invention to the desired site in the blood vessels is via a small diameter medical catheter. The particular catheter employed is not critical provided that polymeric catheter components are compatible with the fluid composition (i.e., the catheter components will not readily degrade in the fluid composition). In this regard, it is preferred to use polyethylene in the catheter components because of its inertness in the presence of the fluid composition described herein. Other materials compatible with the fluid compositions can be readily determined by the skilled artisan and include, for example, other polyolefins, fluoropolymers (e.g., Teflons™), silicone, etc.

One particularly preferred method for the catheter injection of the polymer composition of this invention is described by Greff, et al., U.S. Pat. No. 5,830,178 which issued on Nov. 3, 1998 which patent application is incorporated herein by reference in its entirety.

When a fluid composition comprising a biocompatible polymer is introduced into the blood vessel, the biocompatible solvent diffuses rapidly into the blood and a solid coherent mass forms in situ which precipitate is the water insoluble polymer with any contrast agent encapsulated therein. Without being limited to any theory, it is believed that initially, a soft gel to spongy solid precipitate forms upon contact with the blood which mass adheres to the vascular wall thereby embolizing the blood vessel.

When a fluid composition comprising a biocompatible prepolymer is introduced into the blood vessel, the prepolymer polymerizes in situ to form a solid coherent mass or film with any water insoluble contrast agent encapsulated therein. This mass adheres to the vascular wall thereby embolizing the vessel.

Embolization of the blood vessels can be confirmed by injecting an independent contrast agent such as iopamidol (50:50 mixture with saline) into the blood flow of the aorta. Failure of this contrast agent to reach or flow through the occluded vessels as visualized by fluoroscopy confirms embolization of these blood vessel.

The embolization of blood vessels can be conducted during the surgical repair of the abdominal aortic aneurysm or in a separate surgical procedure conducted prior to the surgical repair. All that is required is identifying an abdominal aortic aneurysm in the patient, identifying the vessels associated with the aneurysm, and introduction of the fluid composition to embolize the blood vessels that cause blood flow with the aneurysm sac after placement of the endovascular prosthesis thereby causing formation of endoleaks.

Utility

The methods described herein are useful for inhibiting the formation of potential endoleaks arising from blood flow to or from blood vessels associated with the aneurysmal sac including the lumbar and inferior mesenteric arteries after endovascular repair of abdominal aortic aneurysms. Accordingly, these methods find use in human and other mammalian subjects requiring endovascular repair of abdominal aortic aneurysms.

Additionally, when a water insoluble contrast agent is employed, the stability of the closure can be monitored weeks, months or even years after sealing by non-invasive fluoroscopic techniques. Resealing of the blood vessels is also facilitated by the presence of the water insoluble contrast agent which permits the clinician to readily identify the site of previously treated blood vessel.

It is contemplated that the procedures set forth above can be employed for inhibiting the formation of potential endoleaks arising from insertion of an endovascular prosthesis at vascular sites other than the abdominal aorta. Such prostheses could be used to repair aneurysms and other vascular diseases at vascular sites such as peripheral vessels.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| atm = | atmospheres |
| cc = | cubic centimeter |
| cm = | centimeter |
| DMSO = | dimethylsulfoxide |
| EVOH = | ethylene vinyl alcohol copolymer |
| g = | gram |
| hrs = | hours |
| IM = | intramuscularly |
| in. = | inch |
| IU = | international units |
| IV = | intravenously |
| kg = | kilogram |
| mg = | milligram |
| min. = | minute |
| mL = | milliliter |
| mm = | millimeter |
| PTFE = | polytetrafluoroethylene |
| sec. = | seconds |
| SQ = | subcutaneously |
| μm = | micron |

Example 1

The purpose of this example is to demonstrate the preparation of a fluid polymer composition useful in the methods of this invention.

Specifically, an EVOH polymer composition was prepared as follows:
Composition
  A) 8 g EVOH;
  B) 30 g tantalum having an average particle size of about 3 μm (narrow size distribution); and
  C) 100 mL DMSO.

Component A) was added to Component C) at 50° C. and stirred for 2 hrs on a hot plate under an argon blanket. To this resulting composition was added Component B and the resulting mixture was mixed until homogeneous.

Example 2

This example illustrates sealing of potential endoleaks which may arise from endovascular repair of an abdominal aortic aneurysm in a dog model. The following illustrates the protocol employed:
Equipment Used
  0.035/0.038 3J Guide Wires (Cook, Bloomington, Ind.)
  5F Angiographic Catheters (Pigtail—Royal Flush II; Cook, Bloomington, Ind.)
  10–14F Introducer Sheaths (Checkflow sheath; Cook, Bloomington, Ind.)
  Angioplasty Balloon Catheters (10×2/10×4/10×6/16×2/18×2/22×2)—(Blue Max and XXL; Meditech, Mass.)
  4 mm PTFE Graft (Gores and Associates, Flagstaff, Ariz.)
  4 mm Aortic Punch (Medtronic, Minneapolis, Minn.)
  Palmaz Stents: P104, P4014, P5014 (Johnson and Johnson Interventional Systems, New Jersey)
  Infusion Catheters (Easy Rider™ 3F, Micro Therapeutics, Irvine, Calif.)
  Microguide Wire (Silver Speed™, Micro Therapeutics, Ivine, Calif.)
  Composition of Example 1
  Contrast Media (Isovue 300) 5F Guiding Catheter (Cordiss, Miami Lakes, Fla.)
Pre-surgical Procedures The animal is fasted 24 hrs prior to surgery and then pre-anesthetized with 0.01 mg/kg Glycopyrrolate SQ followed by anesthetization with a combination of Butorphanol, Xylazine, and Telazol. This combination is given such that 6.6/kg Telazol is given IM. Next, the animal is incubated and connected to Isoflurane gas anesthesia of 1–3%.

A 20 gauge catheter is placed into the cephalic vein of the animal and 0.9% saline is administered intravenously at a rate of 14 mL/kg/hr and then 15 mL blood is collected for CBC liver profile.

A standard sterile surgical preparation and draping is utilized. The right carotid or femoral artery is exposed via vessel cutdown and distal and proximal hemostatic loops are placed. An arteriotomy is then performed and the introducer sheath (10–12F) is advanced into the artery lumen. The sheath and artery is then secured.

After the introducer is placed, the animal is IV heparinized with 100 units of heparin/kg of body weight.

A 5F measuring pigtail catheter is introduced over a standard 0.035 inch, 3 mm "J" guide wire. A flush anteroposterior projection aortogram is obtained with use of contrast media, and the mediolateral diameter of the dog infrarenal aorta is measured with the use of the markers on the pigtail as standardization. A flat film X-ray is required during the contrast arteriography.

In accordance of the measurements of the infrarenal aorta, a Palmaz stent is deployed into the infrarenal aorta on a 10 mm diameter, 4 cm long angioplasty balloon with use of fluoroscopic guidance. Then the infrarenal aorta is overdilated to 1.5–2.0 its measured normal diameter in the dog at 6–8 atm. using a standard pressure gauge for a single inflation lasting 30 sec.

The balloon is removed over a wire and replaced with the measuring pigtail catheter. A repeat aortogram is obtained and the abdominal aortic aneurysm is measured in the animal. A flat film with and without contrast media injections is obtained with all prostheses in the field of view.

A 5F guiding catheter is then introduced and passes to the site of the aneurysm. Under fluoroscopy, contrast is injected to visualize the arteries coming from the aneurysm sac (e.g., lumbar, inferior mesenteric arteries). A 3F microcatheter with a microguide wire passes through the guiding catheter and each identified artery is catherized. The liquid embolic agent is injected into each artery to seal the vessel and prevent any blood flow.

To construct the endovascular graft, a 4 mm PTFE graft is dilated with a 10 mm×6 cm balloon catheter. A balloon expandable Palmaz stent (P104) is secured to the proximal end of the graft with two sutures. This endovascular graft is mounted on 10 mm×6 cm balloon catheters and backloaded into the introducer sheath. The graft is proximally perforated with a 4 mm aortic punch which produces a graft defect that is the source of the potential endoleak. This endograft is placed coaxially within the aneurysms and is dilated with a catheter balloon to a final graft diameter of 9 mm. The balloon is removed and another Palmaz stent (P104) is secured to the distal end of the endograft.

The balloon is again removed over a wire and replaced with the measuring pigtail catheter. A repeat aortogram is obtained and the abdominal aortic aneurysm is measured in the animal. A flat film with and without contrast media injections is obtained with the prosthesis in the field of view. The aortogram shows no leakage of blood through the punch hole defect into the embolized arteries or retrograde flow from the embolized arteries into the aneurysmal sac.

Upon completion, the arteriotomy is closed with interrupted polypropylene sutures and the surrounding tissue is sutured. The animal is allowed to recover before being returned to a cage.

At the conclusion of surgery, the animal is given approximately 25,000 IU/kg procaine and benzathine penicillin SQ.

Post-operatively, the animal receives 325 mg/day of aspirin for 8 weeks and ampicillin 1 g/day for 3 days.

After 1 week, a CT-scan with dye on the dog shows no endoleaks associated with the abdominal aortic aneurysm's endograft.

From the foregoing description, various modifications and changes in the above described methods will occur to those skilled in the art. All such modifications coming within the scope of the appended claims are intended to be included therein.

What is claimed is:

1. A method for in situ embolization of blood vessels associated with an aneurysmal sac which method comprises:
    (a) identifying an abdominal aortic aneurysm in a patient;
    (b) embolizing the lumbar and/or mesenteric arteries associated with the aneurysmal sac wherein said embolization comprises delivering through a microcatheter a sufficient amount of a biocompatible fluid composition to said arteries under conditions where the fluidic composition solidifies thereby embolizing said arteries; and
    (c) subsequently endovascularly repairing said aneurysm by catheter delivery of an endovascular prosthesis to the site of said aneurysm thereby inhibiting blood flow into the aneurysm.

2. The method according to claim 1 wherein the fluid composition comprises a biocompatible polymer and a biocompatible solvent and a contrast agent.

3. The method according to claim 2 wherein said biocompatible polymer is selected from the group consisting of cellulose acetate polymers, ethylene vinyl alcohol copolymers, and polyacrylates.

4. The method according to claim 3 wherein said biocompatible polymer is a cellulose acetate polymer or an ethylene vinyl alcohol copolymer.

5. The method according to claim 2 wherein said biocompatible solvent is selected from the group consisting of dimethylsulfoxide, ethanol, ethyl lactate, and acetone.

6. The method according to claim 5 wherein said biocompatible solvent is dimethylsulfoxide.

7. The method according to claim 2 wherein said contrast agent is a water insoluble contrast agent.

8. The method according to claim 7 wherein said water insoluble contrast agent is selected from the group consisting of tantalum, tantalum oxide, tungsten, and barium sulfate.

9. The method according to claim 7 wherein said water insoluble contrast agent is characterized by having an average particle size of about 10 μm or less.

10. The method according to claim 2 wherein said contrast agent is a water soluble contrast agent.

11. The method according to claim 10 wherein said water soluble contrast agent is selected from the group consisting of metrizamide, iopamidol, iothalamate sodium, iodomide sodium, and meglumine.

12. The method according to claim 1 wherein said composition comprises a biocompatible prepolymer.

13. The method according to claim 12 wherein said biocompatible prepolymer composition further comprises a contrast agent.

14. The method according to claim 13 wherein said contrast agent is a water insoluble contrast agent.

15. The method according to claim 14 wherein said water insoluble contrast agent is selected from the group consisting of tantalum, tantalum oxide, tungsten, and barium sulfate.

16. The method according to claim 14 wherein said water insoluble contrast agent is characterized by having an average particle size of about 10 μm or less.

17. The method according to claim 13 wherein said contrast agent is a water soluble contrast agent.

18. The method according to claim 17 wherein said water soluble contrast agent is selected from the group consisting of metrizamide, iopamidol, iothalamate sodium, iodomide sodium, and meglumine.

19. The method according to claim 13 wherein the biocompatible prepolymer is selected from the group consisting of cyanoacrylates, hydroxyethyl methacrylate and silicone prepolymers.

* * * * *